(12) United States Patent
von Wasielewski et al.

(10) Patent No.: US 7,358,060 B2
(45) Date of Patent: Apr. 15, 2008

(54) METHOD FOR MONITORING AND PROGNOSIS OF DISEASE COURSE OF GASTROINTESTINAL TUMORS

(75) Inventors: Reinhard von Wasielewski, Hannover (DE); Michael Mengel, Lehrte Kolshorn (DE); Rüdiger Ridder, Schriesheim (DE); Peter Martin, Hachenburg (DE)

(73) Assignee: MTM Laboratories, AG, Heidelberg (DE)

( * ) Notice: Subject to any disclaimer, the term of this patent is extended or adjusted under 35 U.S.C. 154(b) by 97 days.

(21) Appl. No.: 10/491,523

(22) PCT Filed: Jan. 31, 2003

(86) PCT No.: PCT/EP03/00968

§ 371 (c)(1),
(2), (4) Date: Jun. 17, 2004

(87) PCT Pub. No.: WO03/065035

PCT Pub. Date: Aug. 7, 2003

(65) Prior Publication Data

US 2005/0084858 A1    Apr. 21, 2005

(30) Foreign Application Priority Data

Feb. 1, 2002    (EP) .................... 02002454

(51) Int. Cl.
*C12Q 1/00*    (2006.01)
*G01N 33/574*    (2006.01)
*G01N 33/48*    (2006.01)

(52) U.S. Cl. ................... 435/7.23; 435/4; 436/64

(58) Field of Classification Search .............. None
See application file for complete search history.

(56) References Cited

U.S. PATENT DOCUMENTS

| | | | |
|---|---|---|---|
| 4,281,061 A * | 7/1981 | Zuk et al. ............. | 435/7.9 |
| 5,965,360 A | 10/1999 | Zain et al. | |
| 6,033,847 A | 3/2000 | Sherr et al. ............. | 435/6 |
| 6,316,208 B1 | 11/2001 | Roberts et al. .......... | 435/7.21 |
| 2003/0157482 A1 | 8/2003 | Keesee et al. ............ | 435/6 |

FOREIGN PATENT DOCUMENTS

WO    WO99/04238    1/1999

OTHER PUBLICATIONS

Tsujie et al., Oncology, vol. 58, p. 126-136, 2000.*
Myung et al., Cancer Letters, vol. 153, p. 129-136, 2000.*
He et al., World J of Gastroenterol, vol. 7, p. 515-21, 2001.*
Takeuchi et al., Clinical Cancer Res, vol. 3, p. 2229-2236, 1997.*
Arber, et al., "Abnormalities in the Expression of Cell Cycle-Related Proteins in Tumors of the Small Bowel", *Cancer Epidemiology, Biomarkers and Prevention*, 8: 1101-05 (1999).
Matthew, et al., "Alterations in Cyclin D1 Expression in Esophageal Squamous Cell Carcinoma in the Indian Population", *J. Cancer Res and Clin Oncol*, 127: 251-57 (2001).
Serrano, et al., "A New Regulatory Motif in Cell-Cycle Control Causing Specific Inhibition of Cyclin D/CDK4", *Nature*, 366: 704-07 (1993).
Nakao et al., "Induction of p16 During Immortalization HPV 16 and 18 and Not During Malignant Transformation" *British J of Cancer* 75(10):1410-1416, 1997.
O'Nions, et al., "p73 Is Over-Expressed In Vulval Cancer Principally As The Δ2 Isoform" *British J. Cancer* 85(10):1551-1556 (Nov. 2001).
Sano, et al., "Overexpression Of P16 and P14ARF Is Associated With Human Papillomavirus Infection In Cervical Squamous Cell Carcinoma And Dysplasia" *Pathology Int.* 52:375-383 (May 2002).
Sano et al., "Expression Status of p16 Protein Is Associated With Human Papillomavirus Oncogenic Potential In Cervical and Genital lesions" *American J. Pathology* 153(6):1741,1998.
Sherr, "The Ink4a/Arf Network In Tumor Suppression" *Nature Reviews Mol. Cell Bio* 2:731-737, (2001).

* cited by examiner

*Primary Examiner*—Shannon Foley
*Assistant Examiner*—Lei Yao
(74) *Attorney, Agent, or Firm*—Howrey LLP; Viola T. Kung

(57) ABSTRACT

The present invention provides a method for diagnosis, monitoring and prognosticating the disease course of gastrointestinal tumors, comprising determining the level of a cyclin dependent kinase inhibitor (CK1) in a sample and diagnosing the disease and/or recurrence of the disease or prognosticating the disease course from the level of said CK1 in the examined tumor cells. Furthermore the present invention provides a method for tailoring a suitable therapy for gastrointestinal tumors. Another aspect of the present invention are test kits for research and diagnostic purposes.

3 Claims, 3 Drawing Sheets

Figure 2

| | | all cases | | | pN0 only | | | pN1+ only | | |
|---|---|---|---|---|---|---|---|---|---|---|
| | Cut-off, definition | n=373 %of positivity | p-value Kaplan-Meier | | n=144 %of positivity | p-value Kaplan-Meier | | n=229 %of positivity | p-value Kaplan-Meier | |
| Localization | limited to one third of stomach but non-proximal | 44% | <0.0001 | | 53% | n. s. | | 39% | <0.0001 | |
| Age 60+ | 60+ years | 58% | 0.0115 | | 58% | n. s. | | 58% | 0.0185 | |
| Gender | male | 62% | n. s. | | 62% | n. s. | | 63% | n. s. | |
| Tumor stage | pT1+2 | 65% | <0.0001 | | 88% | 0.0483 | | 50% | <0.0001 | |
| Nodal stage | pN0 | 39% | <0.0001 | | X | X | | X | X | |
| TUS | IA+IB+II / IIIA+IIIB+IV | 56 / 44% | <0.0001 | | 98 / 2 % | 0.0952 | | 28 / 72 | <0.0001 | |
| Histology | intestinal/diffuse /mixed | 55 / 34 / 11% | n. s. | | 60/33/5% | 0.0978 | | 52/34/14% | n. s. | |
| Grading | 1/2/3 | 4 / 47 / 49% | n. s. | | 7/51/42% | n. s. | | 1/45/54% | n. s. | |
| p53 | >5%+ | 40% | 0.08 | | 35% | n. s. | | 42% | n. s. | |
| Ki-67 (MIB1) | >50%+ | 74% | n. s. | | 79% | n. s. | | 71% | n. s. | |
| CK18 | >5%+ | 92% | n. s. | | 92% | n. s. | | 91% | n. s. | |
| HER2 | Dako Score 1+/2+/3+ | 16% | n. s. | | 15% | n. s. | | 16% | n. s. | |
| S100A4 | >5%+ | 15% | 0.0011 | | 12% | 0.0075 | | 17% | 0.0755 | |
| Cyclin D1 | >5%+ | 27% | n. s. | | 19% | n. s. | | 32% | n. s. | |
| Cyclin D3 | >5%+ | 70% | 0.0294 | | 65% | n. s. | | 73% | n. s. | |
| p27 | >50%+ | 24% | 0.0092 | | 21% | n. s. | | 27% | 0.0832 | |
| p16 | > 33%+ | 38% | <0.0001 | | 36% | <0.0001 | | 38% | 0.0788 | |

Figure 3

| | | all cases | | nodal-negative cases only (pN0) | | | nodal-positive cases only (pN1+) | | |
|---|---|---|---|---|---|---|---|---|---|
| | p-value | RR | 95% CI-RR | p-value | RR | CI-RR | p-value | RR | CI-RR |
| Localization | 0.001 | 1.773 | 1.276 - 2.463 | n. s. | - | - | 0.001 | 1.9 | 1.306 - 2.763 |
| Age | 0.038 | 1.415 | 1.032 - 1.939 | n. s. | - | - | n. s. | - | - |
| Stage, pT | < 0.001 | 1.865 | 1.463 - 2.376 | n. s. | - | - | < 0.001 | 2.02 | 1.523 - 2.681 |
| Stage, pN | < 0.001 | 2.673 | 1.795 - 3.979 | # | # | # | # | # | # |
| p16 | < 0.001 | 1.813 | 1.339 - 2.453 | < 0.001 | 5.503 | 2.672 - 11.335 | 0.03 | 1.464 | 1.039 - 2.063 |

METHOD FOR MONITORING AND PROGNOSIS OF DISEASE COURSE OF GASTROINTESTINAL TUMORS

This application is a National Stage of International Application PCT/EP03/00968, filed Jan. 31, 2003, published Aug. 7, 2003 under PCT Article 21(2) in English; which claims the priority of EP 02002454.3, filed Feb. 1, 2002.

FIELD OF THE INVENTION

The present invention provides a method for monitoring and prognosticating the disease course of gastrointestinal tumors, comprising determining the level of a cyclin dependent kinase inhibitor (CKI) in a sample and diagnosing the disease and/or recurrence of the disease or prognosticating the disease course from the level of said CKI in the examined tumor cells.

BACKGROUND OF THE INVENTION

Gastric cancer is one of the most common cancers in humans. It has been the second most cause of cancer death in the world during the twentieth century. Although decreasing in numbers of incidence over the past years, gastric cancer is still one of the most frequent causes of cancer-related deaths worldwide. Especially in Asia the prevalence of gastric cancer remains higher than in the western world.

Generally the prognosis for gastric cancer is still poor. This is in part due to the fact, that the disease is often diagnosed in a late stage. Furthermore there is a high rate of recurrence after initial therapy of the carcinoma. Therefore an important step in managing gastric cancer is diligent monitoring of the disease course.

First this means to determine the stage of the patients disease. The determination of the stage has a potential prognostic value and can be used to design an optimal therapy. Although in gastric cancer pathological staging is generally preferable over clinical staging, the advantage of clinical staging is, that it does not depend on surgically invasive methods. Thus characterization of the molecular biological properties of a particular tumor could lead to a more specific and efficient therapy. According to the molecular basics of the tumor a therapy could be tailored to avoid recurrence of the disease.

Furthermore monitoring means a close follow up of the disease after initial therapy. On the basis of classical clinical methods the detection of the recurrence of tumors is quite insensitive, so that the disease has reached a progressed stage until it is found. The follow up could as well be carried out on a molecular level, to recognize the recurrence of the disease as early as possible.

There is a series of tools to assess primary diagnosis in tumors such as gastrointestinal tumors. Yet, due to the diversity of the molecular characteristics of tumors, the outcome of detected tumor may vary widely. For assessing prognosis and tailoring an adequate therapy further characterization of the tumors is indispensable. In a series of tumors prediction about the course and the treatment necessary can be made by testing for the level of expression of several tumor markers. Based upon this prognosis it is possible to choose a treatment for the particular tumor to ensure the best chances for the patient gathered with lowest necessary therapeutical burden. For gastric cancer the classic ways of staging and grading of the tumor allow only for a restricted prognosis, so that actually consuming therapies are put through to avoid recurrence of tumors. If the aggressiveness of tumors could be diagnosed on the basis of molecular markers, the therapy could be better suited to the needs of the special case.

Some marker proteins for diagnosing of gastric cancer have been identified to date. For a reliable prognosis of the disease course of gastric cancer in individual patients a series of tumor related cell cycle regulatory proteins have been tested. Yet no correlation between tumor markers and the prognosis of disease course could be found up to now.

Molecular markers being useful for the prognosis of the disease course in a wide range of tumors are the inhibitors of cyclin-dependent kinases. The key role of cyclin dependent kinase inhibitors in the cell cycle is the regulation of the activity of the cyclin dependent kinases. This regulation is brought forth by binding of the CKI to specific binding sites on their respective binding partner cyclin dependent kinases. Two main families of CKI have been identified, the members of which share a high percentage of sequence homology and the binding specificity to their binding partners. The first family of cyclin-dependent kinase inhibitors binds specifically to and inhibits cdk2. The second family in contrast preferentially binds to and inhibits cdk4 and cdk6. Members of the second family of CKI are for example p16, p15, p18 and p19/20.

One candidate marker for the prognosis of disease course, that has proven useful in several tumor types, is the MTS1 protein ($p16^{INK4A}$). p16 has been reported to be valuable marker for assessment of the biological behavior and prognosis for example in nasopharyngeal carcinoma (Wang, L. et al.; 1999, 30 (4), 394-396) and breast cancer. In these cases loss of p16 expression indicates poor prognosis for patients.

Another cyclin-dependent kinase inhibitor p27 turned out to be a candidate for a prognostic marker in tumors.

The level of expression of p27 protein has been described to allow assessment of prognosis in a wide range of tumors (US6180333). In the case of p27, expression of the protein within the samples is associated with better prognosis. The cumulative survival of patients that did not express p27 in the tumor tissue is significantly reduced compared to the patients that showed p27 expression. In gastrointestinal tumors there are hints for correlations between tumor progression and reduced levels of p27 protein (Migaldi M., et al., Pathol Res Pract 2001;197(4):231-6), yet there are difficulties in assessing reliable prognosis in gastrointestinal tumors using this marker protein (Feakins R M., et al., Cancer 2000 Oct. 15;89(8): 1684-91).

Especially in gastrointestinal cancers there is need for molecular markers, that allow for assessment of prognosis, diligent monitoring, building a strategy for therapy and finally sensitive followup.

This is provided by the method claimed according to the present invention.

SUMMARY OF THE INVENTION

The present invention is based on the inventors findings shown in the examples 1-3, that the level of expression of cyclin-dependent kinase inhibitors in tumor samples allows to diagnose and grade the malignancy of a particular tumor, to predict the course of the disease and to follow up the disease after initial therapy. Especially the inventors found that the overexpression CKI is correlated with poor prognosis. Overexpression as used herein shall mean an expression at least two fold elevated in comparison to wild type levels. The present invention furthermore provides a method, that allows to build a strategy for the therapy of tumors according to their molecular properties. According to the present invention the level of cyclin-dependent kinase inhibitors (CKI) can be used as a molecular marker for assessing prognosis, monitoring and the design of a strategy of tumor therapeutics.

BRIEF DESCRIPTION OF THE DRAWINGS

FIG. 2 shows the clinical and pathological characterization of all patients included in a study on the prognostic value of different molecular markers with respect to gastric cancer. Shown are the results of the univariate Kaplan-Meier analysis (p-values) for all patients, nodal-negative cases only (pN0) as well as nodal-positive cases only (pN1+). For experimental details see Example 4.

FIG. 3 show the multivariate analysis (Cox-model) of the clinical patient data and results of immunohistochemical staining of gastrectomies; the Table includes data concerning the factors: localization, age, gender, pT-stage, pN-stage (excluded for subanalysis of nodal-negative and nodal-positive cases), histology, grading, p16. Only the factors which showed a significant prognostic value for survival are listed in this table. Further factors, that have been investigated during the studies are e.g. p53, Ki-67, CK18, Her2, S100A4, Cyclin D1, Cyclin D3 and p27. Abbreviations: RR: relative risk, CI: 95% confidence intervall for relative risk. For experimental details see Example 4.

DETAILED DESCRIPTION OF THE INVENTION

Figure 1:
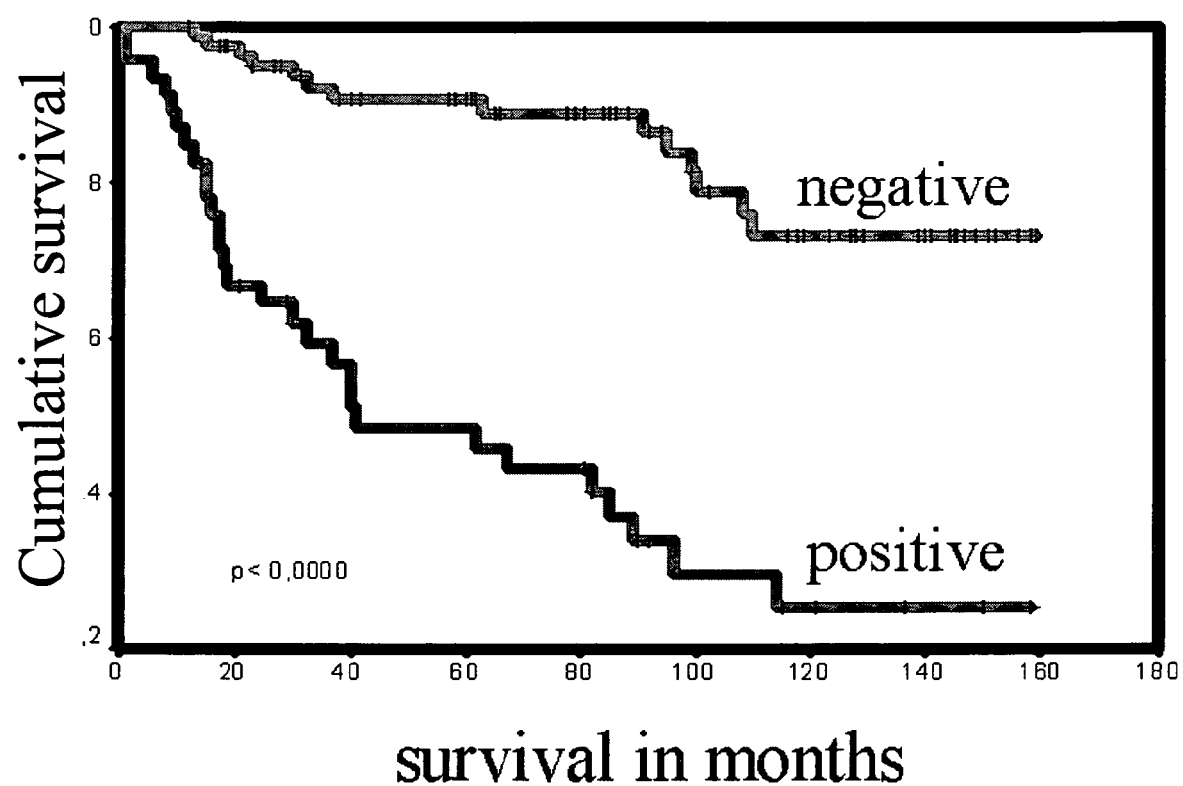
FIG. 1 shows Kaplan-Meier plots correlated to the data of immunohistochemical determination of p16 protein expression in tumor resection samples of node negative tumors of the stomach. On the x-axis of the plot the survival of the individuals is given in months. The y axis gives the cumulative survival. The shown curves are named positive, which means individuals overexpressing p16 protein in the tumor samples, and negative, which means individuals not overexpressing p16 protein in the tumor resections. For the negative samples the cumulative survival of the tested individuals is reduced by about 20% over the tested period of 160 months. In the case of the p16 overexpressing samples the cumulative survival of all tested individuals in contrast is reduced by more than 70% over the same period of time.

Diagnosis as used in the context of the present invention may comprise determining the level of CKI in a sample. Based upon the determined level of CKI in the samples individuals can be subdivided into subgroups. The subgroups may be created according to clinical data, such as e.g. survival, recurrence of disease, frequency of metastases etc., related to the particular level of CKI determined in the samples.

Based upon these subgroups an assessment of prognosis may be done. According to the subgroups the therapy of the individuals affected by the tumors may be tailored.

Monitoring may comprise detecting the level of CKI in samples taken at different points in time and determining the changes in said level. According to said changes the course of the disease can be followed. The course of the disease may be used to select therapy strategies for the particular individual.

Another aspect of diagnosis and monitoring of the disease course according to the present invention may comprise the detection of minimal residual disease. This may comprise for example the detection of a CKI level in one or more body samples following initial therapy of an individual once or at several timepoints. According to the level of CKI detected in the samples one may select a suitable therapy for the particular individual.

Gastrointestinal tumors as used in the context of the present invention are all tumors of the gastrointestinal tract. Tumors may comprise for example neoplasms such as benign and malignant tumors, carcinomas or dysplasias. In a preferred embodiment of the present invention the gastrointestinal tumor is for example a tumor of the esophagus, the stomach, the pancreas, the bile tree, the liver, the small intestine, the colon or the rectum. In a more preferred embodiment the tumor is for example cancer of the esophagus, gastric cancer, cancer of the gallbladder, the pancreas, the liver, the small intestine, the colon or the rectum. The tumors according to the present invention may comprise tumors, which show detectable lymph-node involvement (node positive tumors) as well as tumors, without detectable spread to lymphnodes (node negative tumors). In one preferred embodiment of the invention the gastrointestinal tumors are tumors without detectable spread to lymph nodes.

A sample according to the method of the present invention is any sample of cells or body fluids containing cell cycle regulatory proteins. Such samples may be for example gastrointestinal secretions, stool, bile, biopsies, cell- and tissue-samples. Biopsies as used in the context of the present invention may comprise e.g. resection samples of tumors, tissue samples prepared by endoscopic means or needle biopsies of organs. Furthermore any sample potentially containing the marker molecules to be detected may be a sample according to the present invention. Such samples may comprise for example intact cells, lysed cells or any liquids containing proteins, peptides or nucleic acids. Even solids, to which cells, cell fragments or marker molecules, such as CKI nucleis acids or CKI proteins, may adhere, may be samples according to the present invention. Such solids may comprise for example membranes, glass slides, beads etc.

Preparation of a sample may comprise e.g. obtaining a sample of a tissue, a body fluid, of cells, of cell debris from a patient. According to the present invention preparation of the sample may also comprise several steps of further preparations of the sample, such as preparation of dissections, preparation of lysed cells, preparation of tissue arrays, isolation of polypeptides or nucleic acids, preparation of solid phase fixed peptides or nucleic acids or preparation of beads, membranes or slides to which the molecules to be determined are coupled covalently or non-covalently.

The cyclin-dependent kinase inhibitors according to the present invention may for example be CKI, that do not preferentially bind to cdk2. So CKI according to the present invention may be for example the CKI of the second family. The CKIs used for the method according to the present invention bind preferentially to cdk4 or cdk6 and have low or no binding specificity for cdk2. In one preferred embodiment the CKI may be p16. The present invention may also be applicable to fragments of CKI, functionally equivalent sequences of CKI proteins or nucleic acid sequences coding for functionally equivalent CKI proteins and sequences of CKI proteins or coding for CKI proteins, that are mutated or altered in any way. The mutations according to the present invention may comprise for example insertions, deletions, substitutions or nucleotide mutations.

The method for detection of the level of the cyclin-dependent kinase inhibitor according to the present invention comprises any method, which is suited to detect very small amounts of specific biologically active molecules in biological samples. The detection reaction according to the present invention may be for example a detection either on the level of nucleic acids or on the level of polypeptides.

In one preferred embodiment of the invention the detection of the level of CKI may be carried out by detection of the level of nucleic acids coding for the CKI or fragments thereof present in the sample. The means for detection of nucleic acid molecules are known to those skilled in the art. The procedure for the detection of nucleic acids may for example be carried out by a binding reaction of the molecule to be detected to complementary nucleic acid probes, proteins with binding specificity for the nucleic acids or any other agents specifically recognizing and binding to said nucleic acids. This method may be performed as well in vitro as directly in situ for example in the course of a detecting staining reaction. Another way of detecting the CKI in a sample on the level of nucleic acids performed in the method according to the present invention may be an amplification reaction of nucleic acids, which may be carried out in a quantitative manner such as for example the polymerase chain reaction. In a preferred embodiment of the present invention real time RT PCR may be used to quantify the level of p16 RNA in samples of tumors.

In another preferred embodiment of the invention the detection of the level of CKI may be carried out by determining the level of expression of a protein. The determination of the CKI on the protein level may for example be carried out in a reaction comprising antibodies specific for the detection of the cyclin-dependent kinase inhibitor. The antibodies may be used in many different detection techniques for example in western-blot, ELISA or immunoprecipitation. Generally antibody based detection may be carried out as well in vitro as directly in situ for example in the course of an immuno-histochemical staining reaction. Any other method for determining the amount of particular polypeptides in biological samples may be used according to the present invention.

In a preferred embodiment of the invention the level of CKI is significantly, e.g. at least 2-fold, elevated compared to a non tumorous test sample. In this case the CKI is overexpressed in the sample.

Another aspect of the present invention is a testing kit for performing the method according to the present invention. The kit may be for example a diagnostic kit or a research kit.

A kit according to present invention may comprise:

a) reagents for the detection of the cyclin-dependent kinase inhibitor b) the reagents and buffers commonly used for carrying out the detection reaction, such as buffers, detection-markers, carrier substances and others c) a cyclin-dependent kinase inhibitor sample for carrying out a positive control reaction The reagent for the detection of the cyclin-dependent kinase inhibitor may include any agent capable of binding to the cyclin-dependent kinase inhibitor molecule. Such reagents may include proteins, polypeptides, nucleic acids, peptide nucleic acids, glycoproteins, proteoglycans, polysaccharids or lipids.

The cyclin-dependent kinase inhibitor sample for carrying out a positive control may comprise for example nucleic acids in applicable form, such as solution or salt, peptides in applicable form, tissue section samples or positive cells.

In a preferred embodiment of the invention the detection of the cyclin-dependent kinase inhibitor is carried out on the level of polypeptides. In this embodiment the binding agent may be for example an antibody specific for the cyclin-dependent kinase inhibitor or a fragment thereof.

In an other embodiment of the test kit the detection of the cyclin dependent kinase inhibitor is carried out on the nucleic acid level. In this embodiment of the invention the reagent for the detection may be for example a nucleic acid probe or a primer reverse-complementary to said cyclin-dependent kinase inhibitor nucleic acid.

The method according to the present invention may be used to further characterize detected tumors of the gastrointestinal tract. The method also allows to prognosticate the course of the disease, to design an adequate therapy for the particular tumor and to monitor the disease course in all stages from the primary diagnosis throughout the initial therapy to the follow up. Especially the method according to the invention provides means for staging of tumors without depending on surgically invasive methods. The method according to the invention provides simple to interpret results even in cases, where the classical cytological and histological methods rely on subjective opinions. One advantage of the method is its simplicity in handling, which makes it apt for routine diagnosis and screening tests. Thus the method according to the present invention provides a tool that enhances the diagnosis and monitoring and that allows for assessment of the prognosis of the respective tumor patient. The present invention furthermore provides a tool for subdividing patients into particular subgroups with respect to the prognosis based upon the level of CKI. According to these subgroups of CKI levels the therapy of the individuals may be tailored.

The following examples are given for the purpose of illustration only and are not intended to limit the scope of the invention disclosed herein.

EXAMPLES

Example 1

Determining Correlations Between the Level of Expression of p16 in Stomach Carcinoma Biopsies and the Survival Rate of the Patients In order to determine, whether there is a correlation between the patients outcome and the level of expression of p16 protein detectable in tumors, preparations of 373 gastrectomies were analysed.

The immuno-histochemical detection reaction is carried out as follows (washing steps are included following each single incubation reaction): The paraffin sections are deparaffinized in xylene for 2×10 min. and rehydrogenated using descending dilutions of ethanol (100%, 100%, 90%, 80%, 70%, 50%). The antigens are demasked in 10 mM citrate buffer (pH 6,0) in a waterbath at 95° C. for 40 min. Thereafter the endogeneous peroxidases are inactivated using 3% $H_2O_2$ in PBS. Then the blocking of unspecific binding sites with 1% Casein is carried out at room temperature for 20 minutes. Thereafter the sections are incubated with a monoclonal antibody binding p16 at room temperature for 60 minutes. For the detection of the p16-antibody binding a biotin labelled bioRAM (rabbit-anti-mouse) antibody is added for 30 min. at 37° C. and then avidin-biotinylated peroxidase is added for 30 min. at room temperature. Following, biotinylated thyramid with 0,003% $H_2O_2$ is added (DAKO CSA-Kit). Thereafter avidin-biotinylated alkaline phosphatase is added for 30 min. Then the chromogen neo-fuchsin (pH 8,7) is added for 30 min. A nuclear counterstain is carried out using hemalaun solution.

Alternatively the immuno-histochemical detection reaction is carried out as follows: The paraffin sections are deparaffinized in xylene for 2×10 min. and rehydrogenated using descending dilutions of ethanol (100%, 100%, 90%, 80%, 70%, 50%). The antigens are demasked in 10 mM citrate buffer (pH 6,0) in a waterbath at 95° C. for 40 min. Thereafter the endogeneous peroxidases are inactivated using 3% $H_2O_2$ in PBS. Following the blocking of unspecific binding sites with horse serum at room temperature for 20 minutes, the sections are incubated with a p16-specific monoclonal antibody (Neomarkers, Fremont, Calif., U.S.A.) in the presence of 3% fetal calf serum at room temperature for 45 minutes. For the detection of the p16-antibody binding EnVision System (DAKO A/S, Glostrup, Danmark) comprising anti mouse IgG coupled to a HRP-labeled dextran polymer is added for 30 min. DAB is used thereafter as substrate for the detection reaction and a nuclear counterstain is carried out using Mayer's hemalaun solution.

Following the immuno-histochemical analysis of the tissues the results were compared to the correlating clinical data. Especially Kaplan-Meier plots were done referring to clinical data corresponding to the particular preparations of the tumor resections in correlation to the level of expression of p16 protein found in the samples. The Kaplan Meier plots for the resection samples of node negative tumors are shown in FIG. 1. The plots show, that the total survival of individuals, whose resection samples showed p16 overexpression, is clearly reduced compared to the survival of individuals, which do not show overexpression of p16 in the samples. As a parameter for determination of positive or negative samples the percentage of stained cells were chosen. Samples with more than 33% of the cells in an area stained are said to be overexpressing p16 and thus to be positive. Negative samples not overexpressing p16 show less than 33% of stained cells in the tested area of the samples. For the negative samples, not showing p16 overexpression, the cumulative survival of the tested individuals is reduced by about 20% over the tested period of 160 months. In the case of the p16 overexpressing samples the cumulative survival of all tested individuals in contrast is reduced by more than 70% over the same period of time.

Furthermore the investigations show, that nodal negative cases of carcinoma of the stomach not showing overexpression of p16 protein in the immuno-histochemical analysis have a significantly higher survival rate than those cases showing p16 protein overexpression. This illustrates the correlation between survival of the affected individuals and the level of overexpression of p16 protein in tumor tissues. The example shows that the method according to the present invention provides a means for prognosis of the outcome of patients based on the detection of the level of expression of p16 protein in tumor biopsies.

Example 2

Determining the Correlation Between Survival Rate and p16 mRNA Levels in Tumor Tissues Dissections of tumor biopsies can be semi-quantitatively analysed for the mRNA level of p16 in a in-situ staining reaction. The staining reaction is performed as follows:

The tissue dissections are incubated in ascending ethanol concentrations up to 100% ethanol. After evaporation of the alcohol the dissections are boiled in 10 mM citrate buffer (pH 6,0) for pre-treatment of the tissue. The hybridization mixture is prepared by mixing 50 µl of ready to use hybridisation buffer (DAKO A/S, Glostrup, Danmark) with about 5-10 pmol of the probes. The probes are fluorescein-labelled oligonucleotides of the following sequence:

ccttt taacg tagata taagc cttcc c (SEQ ID NO: 1)

The hybridisation mixture is heated to 95° C. and afterwards equilibrated to 37° C. After the boiling procedure the dissections are incubated with each 50 µl of the hybridisation mixture for 2 hours at 37° C. The dissections are washed in excess volumes of the wash buffers two times in 2×SSC at room temperature for 15 min. and once in 1×SSC at 50° C. for 15 min. Then the dissections are rinsed two times at room temperature in 2×SSC. Following this washing procedure the dissections are incubated for 30 min. with blocking buffer (NEN, Blockingpugger) at room temperature. Then follows 1 hour incubation with a 1:100 diluted (in Blocking buffer, see above) Anti-Fluorescein-AP (DAKO A/S). The dissections are then washed 2 times in 1×PBS/0, 1% Tritonx100 for 10 min. at room temperature, followed by one wash step with 1×PBS, 50 mM $MgCl_2$ (pH 9,2) for 10 min. at room temperature. Then the staining reaction is performed with NBT/BCIP (Sigma) for about 30 min. at room temperature. The staining reaction is stopped by a short incubation with 1 mM EDTA in PBS. Finally the dissections are dipped in $H_2O_{dest}$ and fixed with AquaTex (Merck). Then the stained dissections can be analysed microscopically.

When the histochemical data are compared to clinical data as described in Example 1, the level of p16 RNA detectable in the in situ reaction corresponds to the survival rate of the individuals in a similar manner as shown in Example 1.

Example 3

Determination of Correlation Between Survival Rate and p16 Level in Tumor Tissues using Semiquantitative RT PCR Samples of liver carcinomas are used to determine the level of p16 mRNA using semi-quantitative RT PCR. 34 tumor biopsies are used in this study.

Tumors are collected, snap frozen, and stored at −80° C. They are verified to be composed predominantly of neoplastic cells by histopathological analysis. mRNA is isolated from tumors and patient-matched normal liver tissue using Qiagen reagents (Qiagen, Hilden, Germany), and single-stranded cDNA is synthesized using Superscript II (Life Technologies, Inc.). Quantitative PCR is performed using the 7700 Sequence Detector (Taqman™) and the SYBR Green PCR Master-Mix, as described in the manufacturers manual (Applied Biosystems, Foster City, Calif.).

PCR reactions are performed in 25 µl volumes with a final concentration of 300 nmol for each primer, with 95° C. for 15 sec and 60° C. for 60 sec, for 40 cycles. The following primers are used for quantitative PCR:

p16-A:  TCACT GTGTT GGAGT TTTCT GG (SEQ ID NO: 2)
and p16-B:  GCTTC CCTAG TTCAC AAAAT GC (SEQ ID NO: 3)

The specificity of the PCR products is verified by gel electrophoresis (data not shown).

The data concerning to the level of p16 expression are correlated to clinical data related to the particular tumor samples. The comparison of the p16 levels in the tissues correlates to the outcome of the patients in a similar manner as shown in Example 1.

This illustrates, that the method according to present invention provides a means for determining parameters strictly correlated to the clinical data such as survival and course of the disease on a molecular level. The method may be used according to the present invention to assess prognosis of patients on the basis of molecular biological data.

Example 4

Determination of the Prognostic Value of Different Molecular Markers with Respect to Gastric Cancer The present example makes use of tissue micro arrays for investigation of putative prognostic markers in the course of a comprehensive immunohistochemical analysis of characterized gastric carcinomas.

373 cases with primary gastric cancers fulfilling the following criteria: a) adequate paraffin blocks available, b) UICC-R0 resection, c) pM0 status, d) histologic confirmation of gastric carcinoma e) lack of a history of radiation or chemotherapy, previous gastric resection or second malignancy, e) follow-up data available, f) no perioperative lethality (survival longer than two month after surgery) are examined in the present experiment. All patients underwent gastrectomy with lymph node dissection.

Tissue micro arrays (TMA) for use in the experiments are assembled as follows: all diagnostic H&E slides from each case are reviewed and representative and well preserved tumor tissue is circled on the appropriate slides with a permanent marker. This area of interest is transferred to the cutting side of the corresponding paraffin block and also defined with a permanent marker. Care is taken to choose an area that has been fixed properly and does not show necrosis or scarred tissue. Using a sharpened needle as punching device, tumor tissue cores are taken from each case and stored in a microfuge tube for later use. Finally, the tissue cores of sixty cases are melted together into one new homogenous multiblock that had properties identical to those of any standard paraffin block. Overall, eight tissue micro arrays are prepared containing all study cases. TMA are cut and slides were mounted in the same way as with any conventional paraffin block.

Staining is performed on 2 µm sections of the multiblocks. Slides are dewaxed by xylene, rehydrated by graded alcohol and epitope retrieval is carried out by heating the slides for 20 minutes (100° C.) in 10 mM sodium citrate (pH 6.0). Sections are stained using the Shandon coverplate system in a Tecan Genesis Autostainer (Shandon, Frankfurt a.M., Germany; Tecan, Deisenhofen, Germany). Tissue peroxidase activity is blocked by incubation with 3% hydrogen peroxide for 8 minutes. The primary p27 antibody (novocastra, UK) is applied in a dilution of 1:125. Further molecular markers that are investigated during the studies are e.g. p53, Ki-67, CK18, Her2, S100A4, Cyclin D1 and Cyclin D3.

Biotinylated secondary antibodies are used for the catalyzed signal amplification technique (CSA, Dako). The final color reaction is carried out using new fuchsin as a chromogen, hemalaun as light counterstaining and Kaiser's glycerine (Merck, Darmstadt, Germany) to mount the coverslips.

For the markers six groups are evaluated on a percentual basis: 0-1%; –5%; –10%; –33%; –50% and over 50% of tumor cells showing specific positivity. A preliminary analysis is performed with regard to clinical outcome. On the basis of this preliminary statistical analysis, groups that showed an identical or similar (p>0.2) course are combined. To simplify further evaluation, a bimodal distribution is finally calculated for each parameter including a high-risk and a low-risk group. All further analysis is based on this bimodal distribution.

To investigate associations between expression of the markers and several clinico-pathological and other cell-cycle parameters, data are cross-tabulated and Fisher's exact test is performed (see FIG. 2). The association of staining for p16 with patient survival is evaluated using life tables constructed from survival data with Kaplan-Meier plots,— comparisons between groups are performed with log-rank test. The Cox proportional hazards model (multivariate analysis) is applied to assess the predictive value of the markers, using both a forward and a backward stepwise selection of significant factors (p<0.05). Tests are carried out separately for all cases, or for nodal-negative and nodal-positive status only. All statistical analyses are performed using SPSS version 10.0.7 (SPSS Inc., IL/USA).

For CKI p27 a higher protein expression is associated with a worse prognosis in our series parallel to p16 results. In the present study, p27 does not prove its prognostic value in multivariate regression analysis if CKI p16 is added to the model. Thus, p16 overexpression remains the only immunohistochemical marker protein that provides prognostic information in all cases in addition to localization, age, tumor stage (pT) and nodal stage (pN). Even more strikingly, in a stratified model focusing on nodal-negative patients, p16 overexpression remains the only factor with prognostic value in multivariate analysis (compare FIG. 3).

Thus the results of the present example show that the overexpression of $p16^{INK4A}$ is a powerful prognostic marker molecule. The experiments revealed, that the findings regarding the prognostic value of a series of molecular marker molecules may not be verified analyzing a comprehensive panel of gastric carcinoma samples employing the described high throughput methods.

The cyclin dependent kinase inhibitor p27 interacting with cdk2 that has been included in the present study could not prove any prognostic value. This finding indicates that cyclin dependent kinase inhibitors that do not preferentially bind to cdk4 or cdk6 but e.g. to cdk2 are not as suitable for use in the presented method as CKI preferentially binding to cdk4 or cdk6.

It could be stated that prognostic value for cyclin dependent kinase inhibitors could only be shown for the CKI binding preferentially to cdk4 or cdk6. For these cyclin dependent kinase inhibitors overexpression could be shown to be associated with poor prognosis in gastric carcinomas.

Example 5

Determination of Correlation Between Survival Rate and p19 Level in Carcinomas of the Small Intestine using Semiquantitative RT PCR Samples of carcinomas of the small intestine are used to determine the level of p19 mRNA using semi-quantitative RT PCR. 41 tumor biopsies are used in this study.

Tumors are collected, snap frozen, and stored at –80° C. They are verified to be composed predominantly of neoplastic cells by histopathological analysis. mRNA is isolated from tumors and patient-matched normal intestinal mucosa using Qiagen reagents (Qiagen, Hilden, Germany), and single-stranded cDNA is synthesized using Superscript II (Life Technologies, Inc.). Quantitative PCR is performed using the 7700 Sequence Detector (Taqman™) and the SYBR Green PCR Master-Mix, as described in the manufacturers manual (Applied Biosystems, Foster City, Calif.).

PCR reactions are performed in 25 µl volumes with a final concentration of 300 mmol for each primer, with 95° C. for 15 sec and 60° C. for 60 sec, for 40 cycles.

The specificity of the PCR products is verified by gel electrophoresis (data not shown).

The data concerning the level of p19 expression are correlated to clinical data related to the particular tumor samples. The results show, that the outcome of individuals bearing carcinomas of the small intestine, that overexpress p19 mRNA, is poor in comparison to the outcome of those bearing carcinomas not overexpressing p19 mRNA.

This illustrates, that the method according to present invention provides a means for determining parameters strictly correlated to the clinical data such as survival and course of the disease on a molecular level. The method may be used according to the present invention to assess prognosis of patients on the basis of molecular biological data.

What is claimed is:

1. A method for prognosticating the survival rate of an individual having lymph node-negative gastric cancer comprising detecting the protein expression level of cyclin-dependent kinase inhibitor p16 in a gastric cancer biopsy sample obtained from the individual, wherein the overexpression of the cyclin-dependent kinase inhibitor p16 is correlated with the prognosis of reduced survival rate of the individual.

2. The method of claim 1, wherein the sample is coupled covalently or non-covalently or adhere to a solid.

3. The method of claim 1, wherein the detection of the protein expression level is carried out by means of an antibody specific for the cyclin-dependent kinase inhibitor p16.

* * * * *

SEQUENCE LISTING

<160> NUMBER OF SEQ ID NOS: 3

<210> SEQ ID NO 1
<211> LENGTH: 27
<212> TYPE: DNA
<213> ORGANISM: artificial
<220> FEATURE:
<223> OTHER INFORMATION: Synthetic

<400> SEQUENCE: 1
ccttttaacg tagatataag ccttccc                                    27

<210> SEQ ID NO 2
<211> LENGTH: 22
<212> TYPE: DNA
<213> ORGANISM: artificial
<220> FEATURE:
<223> OTHER INFORMATION: Synthetic

<400> SEQUENCE: 2
tcactgtgtt ggagttttct gg                                         22

<210> SEQ ID NO 3
<211> LENGTH: 22
<212> TYPE: DNA
<213> ORGANISM: artificial
<220> FEATURE:
<223> OTHER INFORMATION: Synthetic

<400> SEQUENCE: 3
gcttccctag ttcacaaaat gc                                         22